United States Patent
Murata et al.

(10) Patent No.: US 10,843,998 B2
(45) Date of Patent: Nov. 24, 2020

(54) METHOD FOR PRODUCING BIS-ACYLOXYLATED EXOMETHYLENE COMPOUND

(71) Applicant: KURARAY CO., LTD., Kurashiki-shi (JP)

(72) Inventors: Yusuke Murata, Tainai (JP); Naoya Minamoto, Kamisu (JP); Mitsumasa Kaneko, Kamisu (JP); Ryosuke Shimizu, Kamisu (JP)

(73) Assignee: KURARAY CO., LTD., Okayama (JP)

( * ) Notice: Subject to any disclaimer, the term of this patent is extended or adjusted under 35 U.S.C. 154(b) by 0 days.

(21) Appl. No.: 16/627,484

(22) PCT Filed: Jul. 23, 2018

(86) PCT No.: PCT/JP2018/027458
§ 371 (c)(1),
(2) Date: Dec. 30, 2019

(87) PCT Pub. No.: WO2019/021993
PCT Pub. Date: Jan. 31, 2019

(65) Prior Publication Data
US 2020/0283367 A1    Sep. 10, 2020

(30) Foreign Application Priority Data

Jul. 24, 2017  (JP) ................... 2017-142559
Dec. 11, 2017  (JP) ................... 2017-236645

(51) Int. Cl.
*C07C 67/05* (2006.01)
*C07C 67/055* (2006.01)

(52) U.S. Cl.
CPC ............ *C07C 67/05* (2013.01); *C07C 67/055* (2013.01)

(58) Field of Classification Search
None
See application file for complete search history.

(56) References Cited

U.S. PATENT DOCUMENTS

2012/0316360 A1  12/2012  Kaneda et al.

FOREIGN PATENT DOCUMENTS

| DE | 1 909 964 | | 9/1970 |
|---|---|---|---|
| GB | 1298326 | * | 11/1972 |
| JP | 4643208 | * | 12/1971 |
| JP | 54-886 B1 | | 1/1979 |
| JP | 2-264781 A | | 10/1990 |
| JP | 11-71327 A | | 3/1999 |
| JP | 4728965 B2 | | 7/2011 |
| JP | 2013-177576 A | | 9/2013 |
| WO | WO 2011/102484 A1 | | 8/2011 |

OTHER PUBLICATIONS

International Search Report dated Oct. 16, 2018 in PCT/JP2018/027458 filed on Jul. 23, 2018, 1 page.
Sanda et al., "Synthesis and Radical Polymerization of Spiroorthocarbonates Bearing exo-Methylene Groups," Macromolecules, 1993, vol. 26, No. 4, pp. 737-743.
Bailey et al.. "Pyrolysis of Esters. XXI. 2-Hydroxymethyl-1,2-butadiene," Journal of Organic Chemistry. Jun. 1962, vol. 27, No. 6, pp. 1975-1978.

* cited by examiner

*Primary Examiner* — Amy C Bonaparte
(74) *Attorney, Agent, or Firm* — Hauptman Ham, LLP

(57) ABSTRACT

A method of producing a bis-acyloxylated exomethylene compound represented by general formula (III), including reacting a monoacyloxylated exomethylene compound represented by general formula (I), a carboxylic acid represented by general formula (II), and oxygen in a liquid phase in the presence of a catalyst and optionally a solvent:

10 Claims, No Drawings

METHOD FOR PRODUCING BIS-ACYLOXYLATED EXOMETHYLENE COMPOUND

TECHNICAL FIELD

The present invention relates to a method of producing a bis-acyloxylated exomethylene compound.

BACKGROUND ART

A bis-acyloxylated exomethylene compound has a 2,2-substituted carbon-carbon unsaturated bond applicable to a radical addition reaction, a hydrosilylation reaction, a hydroformylation reaction or the like and two acyl groups applicable to a saponification reaction, a transesterification reaction or the like, within the same molecule, and thus can be used as a starting material for producing various chemicals due to the reactivity thereof (for example, PTLs 1 and 2).

There are several known methods for producing bis-acyloxylated exomethylene compounds.

For example, NPL 1 describes a method of producing 1,3-diacetoxy-2-methylenepropane by reacting 1,3-dichloro-2-methylenepropane with sodium acetate.

Further, NPL 2 describes a method of producing 1,4-diacetoxy-2-methylenebutane by reacting methyl itaconate with lithium aluminum hydride and then reacting with acetic anhydride.

However, these production methods generate inorganic by-products, which are usually waste material, in equimolar or more to the product.

Therefore, a production method that does not generate an inorganic by-product is desired from the viewpoint of reduction of environmental load reduction.

On the other hand, as a production method which does not generate an inorganic by-product, a method is known in which a terminal olefin compound, a carboxylic acid and oxygen are reacted in a gas phase in the presence of a palladium catalyst to produce a bis-acyloxylated exomethylene compound.

For example, PTL 3 describes a method of producing 1,3-diacetoxy-2-methylenepropane by reacting methallyl acetate, acetic acid, water and oxygen in a gas phase in the presence of a specific catalyst. According to PTL 3, it is described that 1,3-diacetoxy-2-methylenepropane was obtained with a conversion of methallyl acetate of 25% and a selectivity of 95% by passing a mixed gas of nitrogen:oxygen:methallyl acetate:acetic acid:water=40.0:2.0:1.2:5.0:3.0 (mole/hour) per 900 mL of the supported catalyst at 2 atm and subjecting to a gas phase reaction at a reaction temperature of 140° C. (production efficiency of 1,3-diacetoxy-2-methylenepropane 55 g/{L(catalyst)·hr}).

In addition, PTL 4 describes a method of producing 1,3-diacetoxy-2-methylenepropane by passing a mixed gas containing isobutylene, acetic acid and oxygen over a palladium catalyst in a gas phase to react them, and describes that methallyl acetate produced as a by-product is recycled to add to the reaction gas. PTL 4 describes that 1,3-diacetoxy-2-methylenepropane was obtained with a production efficiency of 67 g/{L(catalyst)·hr} by passing a mixed gas of acetic acid:oxygen:isobutylene:methallyl acetate:water vapor=20:10:50:10:10 per 10 mL of the supported catalyst at a rate of 4 L per hour, and performing a gas phase reaction at a reaction temperature of 155° C.

CITATION LIST

Patent Literature

PTL 1: JP 2013-177576 A
PTL 2: JP 2-264781 A
PTL 3: German Patent No. 1909964
PTL 4: JP 47-28965 B

Non-Patent Literature

NPL 1: Macromolecules, 1993, 26 (4), pp. 737-743
NPL 2: Journal of Organic Chemistry 1962, 27 (6), pp. 1975-1978

SUMMARY OF INVENTION

Technical Problem

All of the conventional methods for producing bis-acyloxylated exomethylene compounds which do not generate inorganic by-products are reactions under gas phase conditions. In the gas phase conditions, the oxygen concentration must be kept below the critical oxygen concentration for safety, and it is required to be driven at a low substrate conversion, and thus a substrate recovery apparatus is indispensable. Further, an apparatus for vaporizing a starting material, a reaction tube filled with a catalyst, and an enormous amount of energy for vaporizing a starting material are also required, and there is a lot of room for improvement in terms of production efficiency, facility cost, and energy consumption.

In view of the above circumstances, it is an object of the present invention to provide a method of producing a bis-acyloxylated exomethylene compound which does not generate an inorganic by-product and has improved production efficiency and cost.

Another object of the present invention is to provide a method of producing a bis-acyloxylated exomethylene compound which does not generate an inorganic by-product and has a more improved yield.

Solution to Problem

As a result of intensive studies, the present inventors have found that the production of a bis-acyloxylated exomethylene compound in a specific liquid phase condition allows to solve the above problems. Further repeated studies based on the findings have completed a first invention of the present application.

In addition, as a result of intensive studies, the present inventors have found that, when a monoacyloxylated exomethylene compound, a carboxylic acid and oxygen are reacted under a specific liquid phase condition to produce a bis-acyloxylated exomethylene compound, provision of a portion (remaining) of the total carboxylic acid finally used to the reaction solution in the reaction process, e.g., provision of the carboxylic acid used in a semibatch system, allows to suppress hydrolysis of the monoacyloxylated exomethylene compound of the starting material and the target bis-acyloxylated exomethylene compound by water generated via the reaction, and the yield is further improved. Based on the findings, further studies were repeated to complete a second invention of the present application.

The present invention relates to the following [1] to [11].

[1] A method of producing a bis-acyloxylated exomethylene compound represented by the following general formula (III) (hereinafter sometimes referred to as "bis-acyloxylated exomethylene compound (III)"), including reacting a monoacyloxylated exomethylene compound represented by the following general formula (I) (hereinafter sometimes referred to as "monoacyloxylated exomethylene compound (I)"), a carboxylic acid represented by the following general formula (II) (hereinafter sometimes referred to as "carboxylic acid (II)"), and oxygen in a liquid phase in the presence of a catalyst and optionally a solvent:

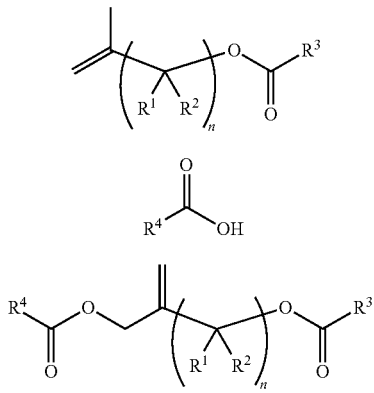

wherein $R^1$ and $R^2$ each independently represent a hydrogen atom, an alkyl group having 1 to 8 carbon atoms and optionally having a substituent, a cycloalkyl group having 3 to 8 carbon atoms and optionally having a substituent, or an aryl group having 6 to 14 carbon atoms and optionally having a substituent; $R^3$ represents a hydrogen atom, an alkyl group having 1 to 8 carbon atoms and optionally having a substituent, a cycloalkyl group having 3 to 8 carbon atoms and optionally having a substituent, an alkenyl group having 2 to 6 carbon atoms and optionally having a substituent, an aryl group having 6 to 14 carbon atoms and optionally having a substituent, an alkoxy group having 1 to 8 carbon atoms and optionally having a substituent, or an aryloxy group having 6 to 14 carbon atoms and optionally having a substituent; $R^4$ represents a hydrogen atom, an alkyl group having 1 to 8 carbon atoms and optionally having a substituent, a cycloalkyl group having 3 to 8 carbon atoms and optionally having a substituent, an alkenyl group having 2 to 6 carbon atoms and optionally having a substituent, or an aryl group having 6 to 14 carbon atoms and optionally having a substituent; and n is an integer of 1 to 8.

[2] The production method according to [1], further including a step of supplying the carboxylic acid to the reaction solution in the reaction process.

[3] The production method according to [2], wherein a whole amount of the carboxylic acid used is continuously supplied to a reactor.

[4] The production method according to any one of [1] to [3], wherein the reaction is carried out in the presence of a solvent.

[5] The production method according to any one of [1] to [4], wherein a total use amount of the solvent and the carboxylic acid is more than 1 mole and 50 moles or less with respect to 1 mole of the monoacyloxylated exomethylene compound.

[6] The production method according to any one of [1] to [5], wherein the solvent is at least one selected from the group consisting of a hydrocarbon, a heterocyclic compound, an ether, a ketone, an ester, an amide, a nitrile, and an alcohol.

[7] The production method according to [6], wherein the solvent is an ester represented by the following general formula (IV):

wherein $R^4$ is as defined above, and $R^5$ is an alkyl group having 1 to 8 carbon atoms and optionally having a substituent or an aryl group having 6 to 14 carbon atoms and optionally having a substituent.

[8] The production method according to [7], wherein $R^4$ is a methyl group and $R^5$ is an alkyl group having 1 to 4 carbon atoms.

[9] The production method according to [7] or [8], wherein a use amount of the carboxylic acid is 0.1 moles or more and 0.6 moles or less with respect to 1 mole of the monoacyloxylated exomethylene compound.

[10] The production method according to any one of [1] to [9], wherein $R^3$ and $R^4$ are a methyl group, and n is 1 or 2.

[11] The production method according to any one of [1] to [10], wherein $R^1$ and $R^2$ are a hydrogen atom.

Advantageous Effects of Invention

According to the first invention of the present application, it is possible to provide a method of producing a bis-acyloxylated exomethylene compound which does not generate an inorganic by-product and provides improved production efficiency and cost.

According to the second invention of the present application, it is possible to provide a method of producing a bis-acyloxylated exomethylene compound which does not generate an inorganic by-product and has a more improved yield.

DESCRIPTION OF EMBODIMENTS

Hereinafter, the present invention will be described in detail.

While a preferred embodiment of the present invention is shown in conjunction with the description of the matters used to specify the invention of the present invention, a combination of two or more of the preferred embodiments of the present invention is also a preferred embodiment of the present invention. Further, several numerical ranges given for the items specified by numerical ranges can provide a preferred embodiment by selectively combining the lower limit value and the upper limit value of them.

In one embodiment according to the first invention of the present application relating to a method of producing the bis-acyloxylated exomethylene compound (III), monoacyloxylated exomethylene compound (I), carboxylic acid (II) and oxygen are reacted in a liquid phase in the presence of a catalyst and optionally a solvent. In one embodiment of the second invention of the present application, a step of supplying the carboxylic acid (II) to the reaction solution in the reaction process is included.

In the above reaction, the monoacyloxylated exomethylene compound (I) is oxidized to undergo dehydration condensation with the carboxylic acid (II) to form water together with the bis-acyloxylated exomethylene compound (III).

The reaction scheme in a preferred embodiment of the present invention is as follows:

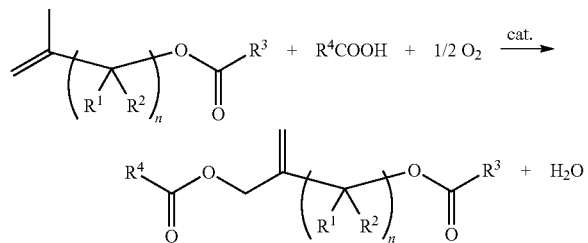

wherein $R^1$ to $R^4$ and n are as defined above.

Employment of the liquid phase conditions allows to reduce each cost of equipment and energy. Also, the study of the present inventors has revealed that, in gas phase conditions, the produced bis-acyloxylated exomethylene compound is adsorbed on the catalyst to inhibit the reaction due to high boiling point thereof, and therefore, the catalyst deactivates at a high temperature for maintaining the gaseous state of the product. In other words, while it is difficult to increase productivity under gas phase conditions, liquid phase conditions are advantageous from a viewpoint of production efficiency and also from a viewpoint of yield.

Further, presence of a step of supplying the carboxylic acid (II) to the reaction solution in the reaction process (i.e., the reaction process of the monoacyloxylated exomethylene compound (I), carboxylic acid (II) and oxygen in the liquid phase) allows to surpress hydrolyzation of the monoacyloxylated exomethylene compound (I) as a starting material or the target bis-acyloxylated exomethylene compound with water generated by the reaction, and improve the yield more.

[Starting Material and Target Product]

Examples of the alkyl group having 1 to 8 carbon atoms represented by $R^1$ and $R^2$ in the monoacyloxylated exomethylene compound (I) and the bis-acyloxylated exomethylene compound (III) include a methyl group, an ethyl group, a n-propyl group, an isopropyl group, a n-butyl group, a sec-butyl group, an isobutyl group, a tert-butyl group, a n-pentyl group, a n-hexyl group, and a n-octyl group.

The alkyl group may have a substituent. Examples of such a substituent include a cycloalkyl group having 3 to 8 carbon atoms, an aryl group having 6 to 14 carbon atoms, an alkoxy group having 1 to 8 carbon atoms, an aryloxy group having 6 to 14 carbon atoms, and a silyl group. When the alkyl group has a substituent, the number of substituents is preferably 1 to 3.

Examples of the silyl group include a trimethylsilyl group, a triethylsilyl group, a tert-butyldimethylsilyl group, a tert-butyldiphenylsilyl group, and a triphenylsilyl group.

The cycloalkyl group having 3 to 8 carbon atoms represented by $R^1$ and $R^2$ may be monocyclic or fused, and examples thereof include a cyclopropyl group, a cyclopentyl group, and a cyclohexyl group.

The cycloalkyl group may have a substituent. Examples of such a substituent include an alkyl group having 1 to 8 carbon atoms, a cycloalkyl group having 3 to 8 carbon atoms, an aryl group having 6 to 14 carbon atoms, an alkoxy group having 1 to 8 carbon atoms, an aryloxy groups having 6 to 14 carbon atoms, and a silyl group described above. When the cycloalkyl group has a substituent, the number of substituents is preferably 1 to 3.

The aryl group having 6 to 14 carbon atoms represented by $R^1$ and $R^2$ may be monocyclic or fused, and examples thereof include a phenyl group, a naphthyl group, an anthryl group, and a phenanthryl group.

The aryl group may have a substituent. Examples of such a substituent include the same as those described above as substituents which may be possessed when $R^1$ and $R^2$ are a cycloalkyl group. When the aryl group has a substituent, the number of substituents is preferably 1 to 3.

From the viewpoint of availability and the like, $R^1$ and $R^2$ are each independently preferably a hydrogen atom or an alkyl group having 1 to 8 carbon atoms, and more preferably a hydrogen atom.

In the monoacyloxylated exomethylene compounds (I) and the bis-acyloxylated exomethylene compounds (III), examples of the alkyl group having 1 to 8 carbon atoms, the cycloalkyl group having 3 to 8 carbon atoms, and the aryl group having 6 to 14 carbon atoms represented by $R^3$ include, for example, the same as those described above for $R^1$ and $R^2$, and the same also applies to the substituents.

Examples of the alkenyl group having 2 to 6 carbon atoms represented by $R^3$ include an ethenyl group (vinyl group), a 1-methylethenyl group, a 1-propenyl group, a 2-propenyl group (allyl group), a 1-methyl-1-propenyl group, a 1-methyl-2-propenyl group, a 1-butenyl group, a 2-butenyl group, and a 3-butenyl group.

The alkenyl group may have a substituent. Examples of such a substituent include the same as those described above as substituents which may be possessed when $R^1$ and $R^2$ are an alkyl group. When the alkenyl group has a substituent, the number of substituents is preferably 1 to 3.

Examples of the alkoxy group having 1 to 8 carbon atoms represented by $R^3$ include a methoxy group, an ethoxy group, a n-propoxy group, an isopropoxy group, a n-butoxy group, an isobutoxy group, a sec-butoxy group, a tert-butoxy group, and a n-pentyloxy group.

The alkoxy group may have a substituent. Examples of such a substituent include the same as those described above as substituents which may be possessed when $R^1$ and $R^2$ are an alkyl group. When the alkoxy group has a substituent, the number of substituents is preferably 1 to 3.

That is, the alkoxy group may be an aralkyloxy group having an aryl group as a substituent, for example. Examples of such an aralkyloxy group include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphthylmethoxy group, and a 2-naphthylmethoxy group.

The aryloxy group having 6 to 14 carbon atoms represented by $R^3$ may be monocyclic or fused, and examples thereof include a phenoxy group, a tolyloxy group, a xyloxy group, and a naphthoxy group.

The aryloxy group may have a substituent. Examples of the substituent include the same as those described above as substituents which may be possessed when $R^1$ and $R^2$ are a cycloalkyl group. When the aryloxy group has a substituent, the number of substituents is preferably 1 to 3.

From the viewpoint of availability and the like, $R^3$ is preferably an alkyl group having 1 to 6 carbon atoms or an alkenyl group having 2 to 6 carbon atoms, more preferably one kind selected from the group consisting of a methyl group, an ethyl group, a n-propyl group, an ethenyl group and a 1-methylethenyl group, still more preferably a methyl group or a 1-methylethenyl group, and most preferably a methyl group.

From the viewpoint of availability and the like, in the monoacyloxylated exomethylene compound (I) and the bis-acyloxylated exomethylene compound (III), n is an integer of 1 to 8, and is preferably an integer of 1 to 4, and more preferably 1 or 2.

In the carboxylic acid (II) and the bis-acyloxylated exomethylene compound (III), examples of the alkyl group having 1 to 8 carbon atoms, the cycloalkyl group having 3 to 8 carbon atoms, the alkenyl group having 2 to 6 carbon atoms, and the aryl group having 6 to 14 carbon atoms represented by $R^4$ are the same as those described above for $R^3$, and the same also applies to the substituents.

From the viewpoint of availability and the like, $R^4$ is preferably an alkyl group having 1 to 8 carbon atoms or an alkenyl group having 2 to 6 carbon atoms, more preferably one kind selected from the group consisting of a methyl group, an ethyl group, a n-propyl group, an ethenyl group and a 1-methylethenyl group, still more preferably a methyl group or a 1-methylethenyl group, and most preferably a methyl group.

[Catalyst]

The catalyst used in the production method of the present invention may be any one that promotes the reaction between the monoacyloxylated exomethylene compound (I) and the carboxylic acid (II), and a catalyst in which a noble metal is supported on a carrier is preferable. The catalyst may be commercially available or may be synthesized by a known method.

Examples of the noble metal include palladium, gold, silver, platinum, rhodium, and ruthenium. These compounds may be used alone or in combination of two or more kinds thereof. Among them, palladium is preferable. The palladium may be a metal palladium or a palladium compound. Examples of the palladium compound include, but are not limited to, palladium chloride, palladium acetate, palladium nitrate, palladium sulfate, sodium palladium chloride, potassium palladium chloride, and barium palladium chloride.

In the case of using a catalyst in which palladium is supported on a carrier, in addition to palladium, a transition metal from Group 8 to Group 11 of the periodic table, such as iron, rhodium, copper and gold, a base metal from Group 12 to Group 15 of the periodic table, such as zinc, indium, tin and bismuth, or a semimetal from Group 13 to Group 16 of the periodic table, such as arsenic and tellurium may be supported on a carrier. These compounds may be used alone or in combination of two or more kinds thereof.

When a catalyst in which a noble metal is supported on a carrier is used, examples of the carrier include a solid oxide such as silica, alumina, zeolite and titanium oxide and a mixture thereof; a polymer compound such as polystyrene, polyethylene, polyamide and cellulose and a mixture thereof, and an activated carbon. These compounds may be used alone or in combination of two or more kinds thereof. Among them, a solid oxide and a mixture thereof or an activated carbon is preferable, silica or alumina is more preferable, and silica is still more preferable.

The particle diameter of the carrier is not particularly limited, but is preferably 10 μm to 10 mm and more preferably 30 μm to 8 mm. When the particle diameter is 10 mm or less, a sufficient amount of the starting material penetrates into the catalyst, so that the reaction is likely to proceed more effectively. When the particle diameter is 10 μm or more, the carrier is more likely to exhibit the function as a carrier.

The use amount of the catalyst is not particularly limited, but preferably 0.01 to 20% by mass and more preferably 0.1 to 10% by mass with respect to the total mass of monoacyloxylated exomethylene compound (I), carboxylic acid (II) and solvent.

[Catalyst Activator]

In the production method of the present invention, a catalyst activator may be added to the catalyst as necessary. Examples of the catalyst activator include hydroxides, nitrates, carboxylates or carbonates of alkali metals such as sodium, potassium and cesium; hydroxides, nitrates, carboxylates or carbonates of alkaline earth metals such as magnesium, calcium and barium. Among them, a salt of carboxylic acid (II) is preferable, an alkali metal salt of carboxylic acid (II) is more preferable, and potassium acetate is still more preferable from the viewpoints of availability and reaction activity.

The use amount of the catalyst activator is not particularly limited, and is preferably 1 to 20% by mass and more preferably 3 to 15% by mass with respect to the catalyst.

The catalyst activator may be used in a state in which the catalyst activator is supported on the catalyst in advance, or may be introduced into a reaction apparatus together with the reaction mixture.

[Solvent]

The production method of the present invention may be carried out in the presence of a solvent. Examples of the solvent include hydrocarbons (including aliphatic hydrocarbons, aromatic hydrocarbons and the like) such as hexane, heptane, methylcyclohexane and benzene; heterocyclic compounds such as pyridine and quinoline; ethers such as diethyl ether, tetrahydrofuran, methyl tert-butyl ether and cyclopentyl methyl ether; ketones such as acetone, methyl ethyl ketone and isobutyl methyl ketone; esters such as carboxylate ester, diethyl carbonate and propylene carbonate; amides such as dimethyl formamide and dimethyl acetamide; nitriles such as acetonitrile and benzonitrile; and alcohols such as methanol, ethanol, isopropyl alcohol and phenol. These may be used alone or in combination of two or more kinds thereof. Among them, carboxylate ester is preferable, and an ester (IV) is more preferable from the viewpoints of production efficiency and yield of the bis-acyloxylated exomethylene compound (III).

In the ester (IV), $R^4$ is the same group as $R^4$ in the carboxylic acid (II) and the bis-acyloxylated exomethylene compound (III).

In the ester (IV), the alkyl group having 1 to 8 carbon atoms or the aryl group having 6 to 14 carbon atoms represented by $R^5$ may be the same as those described above for $R^1$ and $R^2$, for example, and the same applies to the substituents.

From the viewpoints of availability, production efficiency and yield of the bis-acyloxylated exomethylene compound (III), $R^5$ is preferably an alkyl group having 1 to 8 carbon atoms, and more preferably an alkyl group having 1 to 4 carbon atoms.

[Oxygen]

As the oxygen used in the production method of the present invention, atomic and/or molecular oxygen is usable, and molecular oxygen is preferable. When molecular oxygen is used, it is preferably used as a mixed gas with an inert gas such as nitrogen, argon, helium and carbon dioxide. In this case, it is more preferable that the oxygen concentration is adjusted to a range within which the gas does not become explosive composition in a reaction system.

Examples of a method of supplying molecular oxygen or a mixed gas containing molecular oxygen to a reaction system include a method of supplying the mixed gas to a liquid phase portion in a reaction system, a method of supplying the mixed gas to a gas phase portion, and a method of supplying the mixed gas to both a liquid phase portion and a gas phase portion.

When molecular oxygen or a mixed gas containing molecular oxygen is supplied to a reaction system, the oxygen partial pressure is preferably 0.01 atm or more, more preferably 0.1 atm or more, and still more preferably 0.2 atm or more as gauge pressure, and it is preferably 200 atm or less, more preferably 100 atm or less, still more preferably 80 atm or less, and may be 20 atm or less, 10 atm or less, or 8 atm or less.

[Reaction Conditions]

In the production method of the present invention, the total use amount of the solvent and the carboxylic acid (II) is preferably greater than 1 mole and 50 moles or less, more preferably 1.5 moles or more and 35 moles or less, and still more preferably 2 moles or more and 10 moles or less, with respect to 1 mole of the monoacyloxylated exomethylene compound (I). When the total use amount is greater than 1 mole, the hydrolysis of the monoacyloxylated exomethylene compound (I) and the bis-acyloxylated exomethylene compound (III) by water generated by the reaction is suppressed, and the production efficiency and the yield of the bis-acyloxylated exomethylene compound (III) are further improved. When the total use amount is 50 moles or less, the recovery step of excess solvent and carboxylic acid (II) is shortened, which is economically advantageous.

The present inventors have found that the employment of the ester (IV) as a solvent in the production method of the present invention allows to provide a high production efficiency and a high yield even when the use amount of the carboxylic acid (II) is reduced to 0.1 moles or more and 0.6 moles or less per 1 mole of the monoacyloxylated exomethylene compound (I). When the use amount of the carboxylic acid (II) is within the above range, it is industrially very advantageous due to obtainability of both suppression of apparatus corrosion and simplification of introduction of the starting materials.

Reaction conditions such as reaction temperature, reaction pressure, and reaction time in the production method of the present invention may be appropriately set depending on the kind and combination of the monoacyloxylated exomethylene compound (I), the carboxylic acid (II) and the solvent, the catalyst composition and the like, but are not particularly limited thereto. For example, the reaction temperature is preferably in the range of 80 to 200° C. When the reaction temperature is 80° C. or higher, the reaction rate is not too slow, and the bis-acyloxylated exomethylene compound (III) generates efficiently. On the other hand, by setting the reaction temperature to 200° C. or lower, side reactions including combustion are hardly caused, the bis-acyloxylated exomethylene compound (III) generates efficiently, and corrosion of the reaction apparatus with a carboxylic acid is also able to be suppressed.

The reaction system in the production method of the present invention may be either a continuous system or a batch system, and is not particularly limited. When, for example, a batch system is employed as the reaction system, the catalyst may be charged together with the starting material in the reaction apparatus, and when a continuous system is employed as the reaction system, for example, the catalyst may be filled in advance in the reaction apparatus or may be continuously charged together with the starting material in the reaction apparatus. The catalyst may be used in any form of a fixed bed, a fluidized bed, or a suspended bed.

One embodiment according to the second invention of the present application includes a step for supplying carboxylic acid (II) to a reaction liquid in a reaction process of a monoacyloxylated exomethylene compound (I), a carboxylic acid (II) and an oxygen in a liquid phase, i.e., a state in which a reaction with the carboxylic acid (II) and the oxygen is completed with respect to a part of the monoacyloxylated exomethylene compound (I), while the unreacted monoacyloxylated exomethylene compound (II) remains. The step is possible by supplying the carboxylic acid (II) to a reactor in a semibatch system, and more specifically, by supplying the carboxylic acid (II) to a reactor continuously and/or in a plurality of batches without substantially removing the bis-acyloxylated exomethylene compound (III) from a reactor in the above reaction process (for example, without removing 5% by mass or more of the bis-acyloxylated methylene compound (III) finally obtained from a reactor in the above reaction process).

In the above, a whole amount of the carboxylic acid (II) to be used may be continuously supplied to a reactor or a whole amount of the carboxylic acid (II) to be used may be supplied to a reactor in a plurality of batches. For example, the reaction may be started with a portion of the carboxylic acid (II) to be used previously contained in a reactor, and then the remainder may be supplied to a reactor continuously and/or in a plurality of batches. From the viewpoints of operability and yield, it is preferable to continuously supply a whole amount of the carboxylic acid (II) to be used to a reactor.

When a system not including the step of supplying the carboxylic acid (II) to the reaction solution in the above reaction process, such as a system in which after starting materials such as the monoacyloxylated exomethylene compound (I), the carboxylic acid (II) and the catalyst are charged in a reactor all at once, the above reaction is started in a batch system, or a system in which the above reaction is started in a continuous system while supplying starting materials such as the monoacyloxylated exomethylene compound (I) and the carboxylic acid (II) to the upstream part of a tubular reactor, is employed, the monoacyloxylated exomethylene compound (I) and the target bis-acyloxylated exomethylene compound (III) are hydrolyzed by the water generated by the reaction, so that the yield of the bis-acyloxylated exomethylene compound (III) tends to decrease. However, the step of supplying the carboxylic acid (II) to the reaction solution in the reaction process allows to improve the yield.

In one embodiment according to the second invention of the present application, there is no particular limitation on the supply system of other starting materials other than the carboxylic acid (II) such as the monoacyloxylated exomethylene compound (I), and the reaction may be started after supplying the reaction mixture to a reactor at once, or continuously supplied to a reactor. When the reaction is started after supplying to a reactor at once, the catalyst may be charged together with the monoacyloxylated exomethylene compound (I) and the like collectively, and when continuously supplied to a reactor, the catalyst may be filled in advance in the reaction apparatus or may be continuously charged with the monoacyloxylated exomethylene compound (I) or the like in the reaction apparatus. The catalyst may be used in any form of a fixed bed, a fluidized bed, or a suspended bed.

The bis-acyloxylated exomethylene compound (III) produced by the production method of the present invention can be isolated by separating the catalyst and then purifying the reaction solution. The means for purification is not particularly limited, but distillation method, extraction method, or column chromatography can be used. These methods may be carried out in combination. Among them, distillation method or extraction method is preferably used.

The starting material and solvent separated by the purification can be used again for the reaction. Also, the separated catalyst can be used for the reaction again.

EXAMPLES

Hereinafter, the present invention will be described in more detail with reference to Examples, but the present invention is not limited to these Examples.

[Analysis Condition 1]

Analysis of the solution (reaction mixture) after the reaction in the following Examples 1 to 8 and Comparative Examples 1 and 2 was carried out using a gas chromatograph GC2014 (FID detector, manufactured by Shimadzu Corporation) and a capillary column (DB-1, length 30 m, inner diameter 0.25 mm, thickness 0.25 µm, manufactured by Agilent Technologies Co., Ltd.) under the following conditions.

Column temperature: 50° C. (5 min)→10° C./min→250° C. (5 min)
FID temperature: 250° C.
Inlet temperature: 250° C.
Carrier gas: helium
Make-up gas: helium
Injection: 0.2 µL
Column gas flow rate: 0.38 mL/min
Split ratio: 20

[Analysis Condition 2]

Analysis of the solution (reaction mixture) after the reaction in the following Examples 9 and 10 was carried out using a gas chromatograph GC2014 (FID detector, manufactured by Shimadzu Corporation) and a capillary column (DB-1, length 30 m, inner diameter 0.25 mm, thickness 0.25 µm, manufactured by Agilent Technologies Co., Ltd.) under the following conditions.

Column temperature: 50° C. (5 min)→10° C./min→250° C. (5 min)
FID temperature: 250° C.
Inlet temperature: 250° C.
Carrier gas: helium
Make-up gas: helium
Injection: 0.2 µL
Column gas flow rate: 1.02 mL/min
Purge flow rate: 3.0 mL/min
Split ratio: 100

Conversion

The ratio of the consumed mass to the charged mass of the monoacyloxylated exomethylene compound (I) analyzed under the above conditions was calculated as a conversion by using the following formula.

Conversion (%)={(the mass of the consumed monoacyloxylated exomethylene compound (I))/(the mass of the charged monoacyloxylated exomethylene compound (I))}×100

Selectivity

The ratio of the mass of the produced bis-acyloxylated exomethylene compound (III) to the mass of the consumed monoacyloxylated exomethylene compound (I) analyzed under the above conditions was calculated using the following formula as a selectivity.

Selectivity (%)={(the mass of the produced bis-acyloxylated exomethylene compound (III))/(the mass of the consumed monoacyloxylated exomethylene compound (I))}×100

Reference Example 1: Preparation of Catalyst 1

250 mL of a silica carrier (5 mm) was immersed in an aqueous solution containing 4.00 g (13.6 mmol) of sodium tetrachloropalladium acid and 2.80 g (6.8 mmol) of tetrachloroauric acid tetrahydrate, and the whole amount of the aqueous solution was absorbed into the silica carrier. Then, 200 mL of an aqueous solution containing 16 g (131 mmol) of sodium metasilicate was added to the resulting silica carrier, and the resultant was allowed to stand for 20 hours. Thereafter, 9.50 g (190 mmol) of hydrazine monohydrate was added thereto to reduce the palladium salt and the gold salt to metal. After the reduction, the obtained catalyst was washed with water, and then dried at 110° C. for 4 hours. Thereafter, the above carrier containing metallic palladium was charged into an aqueous solution containing 13.34 g (136 mmol) of potassium acetate, and after absorbing the whole liquid, the carrier was dried at 110° C. for 4 hours to prepare catalyst 1.

Reference Example 2: Preparation of Catalyst 2

In an aqueous solution containing 4.00 g (13.6 mmol) of sodium tetrachloropalladium acid and 3.90 g (9.5 mmol) of tetrachloroauric acid tetrahydrate, 250 mL of a silica carrier (5 mmφ) was immersed, and the whole amount of the aqueous solution was absorbed into the silica carrier. Then, 200 mL of an aqueous solution containing 16 g (131 mmol) of sodium metasilicate was added to the resulting silica carrier, and the resultant was allowed to stand for 20 hours. Thereafter, 9.50 g (190 mmol) of hydrazine monohydrate was added thereto to reduce the palladium salt and the gold salt to metal.

After the reduction, the obtained catalyst was washed with water, and then dried at 110° C. for 4 hours. Thereafter, the above carrier containing metallic palladium was charged into an aqueous solution containing 13.34 g (136 mmol) of potassium acetate, and after absorbing the whole liquid, the carrier was dried at 110° C. for 4 hours to prepare catalyst 2.

Example 1

1.3 g of catalyst 1, 46.0 g (766 mmol) of acetic acid and 3.0 g (23 mmol) of isoprenyl acetate were charged to an electromagnetic stirring autoclave having an internal volume of 100 mL provided with a gas inlet and a sampling port, and the inside of the autoclave was brought to 20 atm (gauge pressure) with a mixed gas of oxygen/nitrogen=8/92 (molar ratio), and then the temperature in the autoclave was raised to 120° C. with stirring. Then, the reaction was carried out for 5 hours while flowing a mixed gas at a flow rate of 200 mL/min and maintaining 90 atm (gauge pressure) with a mixed gas of oxygen/nitrogen=8/92 (molar ratio). The conversion of isoprenyl acetate was 83%, and the selectivity to 1,4-diacetoxy-2-methylenebutane was 85%. The yield of 1,4-diacetoxy-2-methylenebutane was 3.1 g (17 mmol), and the production efficiency (yield per unit time and catalyst unit mass) of 1,4-diacetoxy-2-methylenebutane was 0.48 g (product)/{g(catalyst)·hr}.

Example 2

The reaction was carried out in the same manner as in Example 1 except that 40 g (666 mmol) of acetic acid and 9 g (70 mmol) of isoprenyl acetate were used. The conversion of isoprenyl acetate was 80%, and the selectivity to 1,4-diacetoxy-2-methylenebutane was 82%. The yield of 1,4-diacetoxy-2-methylenebutane was 8.6 g (46 mmol), and the production efficiency of 1,4-diacetoxy-2-methylenebutane was 1.34 g (product)/{g(catalyst)·hr}.

Example 3

1.3 g of catalyst 2, 40 g (666 mmol) of acetic acid and 8 g (70 mmol) of methallyl acetate were charged to an electromagnetic stirring autoclave having an internal volume of 100 mL provided with a gas inlet and a sampling port, and the inside of the autoclave was brought to 20 atm (gauge pressure) with a mixed gas of oxygen/nitrogen=8/92 (molar ratio), and then the temperature in the autoclave was raised to 140° C. with stirring. Then, the reaction was carried out for 5 hours while flowing a mixed gas at a flow rate of 200 mL/min and maintaining 90 atm (gauge pressure) with a mixed gas of oxygen/nitrogen=8/92 (molar ratio). The conversion of methallyl acetate was 99%, and the selectivity to 1,3-diacetoxy-2-methylenepropane was 61%. The yield of 1,3-diacetoxy-2-methylenepropane was 7.3 g (42 mmol), and the production efficiency of 1,3-diacetoxy-2-methylenepropane was 1.14 g (product)/{g(catalyst)·hr}.

Comparative Example 1

17 g (about 30 mL) of catalyst 1 was packed into a stainless steel reaction tube having an inner diameter of 23 mm and a length of 20 cm, and then isoprenyl acetate, acetic acid, oxygen and nitrogen were flowed through the reaction tube at a rate of 15 L/hr in a volume ratio of isoprenyl acetate:acetic acid:oxygen:nitrogen=28:3:8:61, and the reaction was carried out at 165° C. After 4 hours, the composition at the reaction tube outlet was analyzed, and the production rate of 1,4-diacetoxy-2-methylenebutane was 0.032 g (product)/{g(catalyst)·hr}, and the yield of 1,4-diacetoxy-2-methylenebutane to isoprenyl acetate introduced into the reaction tube was 2.3%. The results show that the gas phase reaction is less productive than the liquid phase reaction.

Comparative Example 2

The reaction was carried out in the same manner as in Comparative Example 1 except that the reaction temperature was changed to 190° C. The production rate of 1,4-diacetoxy-2-methylenebutane was 0.015 g (product)/{g(catalyst)·hr}, and the yield of 1,4-diacetoxy-2-methylenebutane to isoprenyl acetate introduced into the reaction tube was 0.5%.

Thereafter, only nitrogen was allowed to flow through the reaction tube at a rate of 15 NL/hr for 1 hour at 190° C. under atmospheric pressure, then the reaction tube was cooled to room temperature, and the catalyst was taken out therefrom. When the catalyst after the reaction was observed, the catalyst which was grayish before the reaction turned brown.

Example 4

The reaction was carried out in the same manner as in Example 3, except that 3.2 g (53.3 mmol) of acetic acid and 6.0 g (52.6 mmol) of methallyl acetate were used, and 40 g (399 mmol) of heptane was used as a solvent. The conversion of methallyl acetate was 82%, and the selectivity to 1,3-diacetoxy-2-methylenepropane was 60%. The yield of 1,3-diacetoxy-2-methylenepropane was 4.5 g (26 mmol), and the production efficiency of 1,3-diacetoxy-2-methylenepropane was 0.70 g (product)/{g(catalyst)·hr}.

Example 5

The reaction was carried out in the same manner as in Example 3, except that 4.5 g (74.9 mmol) of acetic acid and 17.0 g (148.9 mmol) of methallyl acetate were used, and 26.0 g (295 mmol) of ethyl acetate was used as a solvent. The conversion of methallyl acetate was 78%, and the selectivity to 1,3-diacetoxy-2-methylenepropane was 80%. The yield of 1,3-diacetoxy-2-methylenepropane was 16.0 g (93 mmol), and the production efficiency of 1,3-diacetoxy-2-methylenepropane was 2.50 g (product)/{g(catalyst)·hr}.

Example 6

The reaction was carried out in the same manner as in Example 3, except that 5.5 g (91.6 mmol) of acetic acid and 20.7 g (181 mmol) of methallyl acetate were used, and 20.7 g (178 mmol) of isobutyl acetate was used as a solvent. The conversion of methallyl acetate was 80%, and the selectivity to 1,3-diacetoxy-2-methylenepropane was 86%. The yield of 1,3-diacetoxy-2-methylenepropane was 21.5 g (125 mmol), and the production efficiency of 1,3-diacetoxy-2-methylenepropane was 3.36 g (product)/{g(catalyst)·hr}.

Example 7

The reaction was carried out in the same manner as in Example 1, except that 4.3 g (72 mmol) of acetic acid and 18.2 g (142 mmol) of isoprenyl acetate were used, and 25 g (284 mmol) of ethyl acetate was used as a solvent. The conversion of isoprenyl acetate was 70%, and the selectivity to 1,4-diacetoxy-2-methylenebutane was 82%. The yield of 1,4-diacetoxy-2-methylenebutane was 15.2 g (82 mmol), and the production efficiency of 1,4-diacetoxy-2-methylenebutane was 2.37 g (product)/{g(catalyst)·hr}.

Example 8

The reaction was carried out in the same manner as in Example 3, except that 15.8 g (263 mmol) of acetic acid and 30.0 g (263 mmol) of methallyl acetate were used. The conversion of methallyl acetate was 75%, the selectivity to 1,3-diacetoxy-2-methylenepropane was 23%, the yield of 1,3-diacetoxy-2-methylenepropane was 7.8 g (45 mmol), and the production efficiency of 1,3-diacetoxy-2-methylenepropane was 1.22 g (product)/{g(catalyst)·hr}.

The results of Examples 1 to 8 and Comparative Examples 1 and 2 described above are shown in Table 1 below.

TABLE 1

| | Reaction phase | Catalyst | Monoacyloxylated exomethylene compound (I) | Solvent | Molar ratio *1 | Conversion *2 | Selectivity *3 | Production efficiency *4 |
|---|---|---|---|---|---|---|---|---|
| Example 1 | Liquid phase | Catalyst 1 | Isoprenyl acetate | — | 1/33/0 | 83% | 85% | 0.48 |
| Example 2 | | | | — | 1/9.5/0 | 80% | 82% | 1.34 |
| Example 3 | | Catalyst 2 | Methallyl acetate | — | 1/9.5/0 | 99% | 61% | 1.14 |
| Example 4 | | | | Heptane | 1/1/7.5 | 82% | 60% | 0.70 |
| Example 5 | | | | Ethyl acetate | 1/0.5/2 | 78% | 80% | 2.50 |
| Example 6 | | | | Isobutyl acetate | 1/0.5/2 | 80% | 86% | 3.36 |
| Example 7 | | Catalyst 1 | Isoprenyl acetate | Ethyl acetate | 1/0.5/2 | 70% | 82% | 2.37 |
| Example 8 | | Catalyst 2 | Methallyl acetate | — | 1/1/0 | 75% | 23% | 1.22 |
| Comparative Example 1 | Gas phase | Catalyst 1 | Isoprenyl acetate | — | 28/3/— | Yield 2.3% | | 0.032 |
| Comparative Example 2 | | | | — | 30/17/— | Yield 0.5% | | 0.015 |

*1: Monoacyloxylated exomethylene compound (I)/carboxylic acid (II)/solvent
*2: Conversion of monoacyloxylated exomethylene compound (I)
*3: Selectivity to bis-acyloxylated exomethylene compound (III)
*4: Production efficiency of bis-acyloxylated exomethylene compound (III) [g(product)/{g(catalyst) hr}]

Example 9

1.3 g of catalyst 2, 30.0 g (263 mmol) of methallyl acetate were charged to an electromagnetic stirring autoclave having an internal volume of 100 mL provided with a gas inlet and a sampling port, and the inside of the autoclave was brought to 20 atm (gauge pressure) with a mixed gas of oxygen/nitrogen=8/92 (molar ratio), and then the temperature in the autoclave was raised to 140° C. with stirring. Then, acetic acid was continuously supplied at 3.16 g/hr and the reaction was carried out for 5 hours while flowing a mixed gas at a flow rate of 200 mL/min and maintaining 90 atm (gauge pressure) with a mixed gas of oxygen/nitrogen=8/92 (molar ratio) (total use amount of acetic acid is 15.8 g (263 mmol)).

The conversion of methallyl acetate was 70%, the selectivity to 1,3-diacetoxy-2-methylenepropane was 39%, and the yield of 1,3-diacetoxy-2-methylenepropane was 27%.

Example 10

1.3 g of catalyst 2, 17.0 g (149 mmol) of methallyl acetate, and 26.0 g (295 mmol) of ethyl acetate as a solvent were charged to an electromagnetic stirring autoclave having an internal volume of 100 mL provided with a gas inlet and a sampling port, and the inside of the autoclave was brought to 20 atm (gauge pressure) with a mixed gas of oxygen/nitrogen=8/92 (molar ratio), and then the temperature in the autoclave was raised to 140° C. with stirring. Then, acetic acid was continuously supplied at 0.90 g/hr and the reaction was carried out for 5 hours while flowing a mixed gas at a flow rate of 200 mL/min and maintaining 90 atm (gauge pressure) with a mixed gas of oxygen/nitrogen=8/92 (molar ratio) (total use amount of acetic acid is 4.5 g (74.9 mmol)).

The conversion of methallyl acetate was 88%, the selectivity to 1,3-diacetoxy-2-methylenepropane was 90%, and the yield of 1,3-diacetoxy-2-methylenepropane was 79%.

The results of Examples 9 and 10 described above are shown in Table 2 below.

TABLE 2

| | Reaction phase | Solvent | Supply system of carboxylic acid (II) | Molar ratio *5 | Conversion *6 | Selectivity *7 | Yield |
|---|---|---|---|---|---|---|---|
| Example 9 | Liquid phase | None | Semibatch | 1/1/0 | 70% | 39% | 27% |
| Example 10 | Liquid phase | Ethyl acetate | Semibatch | 1/0.5/2 | 88% | 90% | 79% |

*5: Monoacyloxylated exomethylene compound (I)/carboxylic acid (II)/solvent
*6: Conversion of monoacyloxylated exomethylene compound (I)
*7: Selectivity to bis-acyloxylated exomethylene compound (III)

INDUSTRIAL APPLICABILITY

The production method of the present invention provides the bis-acyloxylated exomethylene compound with high yield, high production efficiency and high cost performance without generating an inorganic by-product. The resulting bis-acyloxylated exomethylene compound is usable as a starting material for producing a variety of industrially useful compounds.

The invention claimed is:
1. A method of producing a bis-acyloxylated exomethylene compound of formula (III), the method comprising:
reacting a monoacyloxylated exomethylene compound of formula (I), a carboxylic acid of formula (II), and oxygen in a liquid phase in the presence of a noble metal catalyst and optionally a solvent:

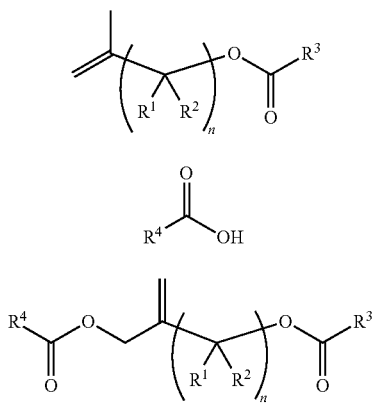

wherein $R^1$ and $R^2$ each independently represent a hydrogen atom, an alkyl group having 1 to 8 carbon atoms and optionally having a substituent, a cycloalkyl group having 3 to 8 carbon atoms and optionally having a substituent, or an aryl group having 6 to 14 carbon atoms and optionally having a substituent; $R^3$ represents a hydrogen atom, an alkyl group having 1 to 8 carbon atoms and optionally having a substituent, a cycloalkyl group having 3 to 8 carbon atoms and optionally having a substituent, an alkenyl group having 2 to 6 carbon atoms and optionally having a substituent, an aryl group having 6 to 14 carbon atoms and optionally having a substituent, an alkoxy group having 1 to 8 carbon atoms and optionally having a substituent, or an aryloxy group having 6 to 14 carbon atoms and optionally having a substituent; $R^4$ represents a hydrogen atom, an alkyl group having 1 to 8 carbon atoms and optionally having a substituent, a cycloalkyl group having 3 to 8 carbon atoms and optionally having a substituent, an alkenyl group having 2 to 6 carbon atoms and optionally having a substituent, or an aryl group having 6 to 14 carbon atoms and optionally having a substituent; and n is an integer of 1 to 8.

2. The method according to claim 1, wherein the reacting takes place in a reactor and further comprising continuously supplying the carboxylic acid to the reactor during the reacting.

3. The method according to claim 1, wherein the reacting is carried out in the presence of a solvent.

4. The method according to claim 1, wherein a total amount of the solvent and the carboxylic acid is more than 1 mole and 50 moles or less with respect to 1 mole of the monoacyloxylated exomethylene compound.

5. The method according to claim 1, wherein the solvent is at least one selected from the group consisting of a hydrocarbon, a heterocyclic compound, an ether, a ketone, an ester, an amide, a nitrile, and an alcohol.

6. The method according to claim 5, wherein the solvent is an ester of formula (IV):

wherein $R^4$ represents a hydrogen atom, an alkyl group having 1 to 8 carbon atoms and optionally having a substituent, a cycloalkyl group having 3 to 8 carbon atoms and optionally having a substituent, an alkenyl group having 2 to 6 carbon atoms and optionally having a substituent, or an aryl group having 6 to 14 carbon atoms and optionally having a substituent, and $R^5$ is an alkyl group having 1 to 8 carbon atoms and optionally having a substituent or an aryl group having 6 to 14 carbon atoms and optionally having a substituent.

7. The method according to claim 6, wherein, in formula (IV), $R^4$ is a methyl group and $R^5$ is an alkyl group having 1 to 4 carbon atoms.

8. The method according to claim 6, wherein an amount of the carboxylic acid used in the reacting is 0.1 moles or more and 0.6 moles or less with respect to 1 mole of the monoacyloxylated exomethylene compound.

9. The method according to claim 1, wherein $R^3$ and $R^4$ are a methyl group, and n is 1 or 2.

10. The method according to claim 1, wherein $R^1$ and $R^2$ are a hydrogen atom.

* * * * *